(12) United States Patent
Weinstein (10) Patent No.: US 7,795,216 B2
(45) Date of Patent: Sep. 14, 2010

(54) METHODS FOR PROMOTING COMPOSITE TISSUE REGENERATION AND USES THEREOF

(75) Inventor: David E. Weinstein, Dobbs Ferry, NY (US)

(73) Assignee: Glia Med, Inc., Dobbs Ferry, NY (US)

(*) Notice: Subject to any disclaimer, the term of this patent is extended or adjusted under 35 U.S.C. 154(b) by 504 days.

(21) Appl. No.: 11/679,764

(22) Filed: Feb. 27, 2007

(65) Prior Publication Data

US 2009/0093528 A1   Apr. 9, 2009

Related U.S. Application Data

(60) Provisional application No. 60/743,749, filed on Mar. 24, 2006.

(51) Int. Cl.
*A61K 38/00* (2006.01)
*A61K 31/41* (2006.01)

(52) U.S. Cl. .................................. 514/12; 514/361

(58) Field of Classification Search ............ 514/12, 514/361
See application file for complete search history.

(56) References Cited

U.S. PATENT DOCUMENTS

| 6,809,107 | B1 | 10/2004 | Kanojia | |
|---|---|---|---|---|
| 7,189,746 | B2 * | 3/2007 | Weinstein | 514/364 |
| 2004/0092440 | A1 | 5/2004 | Weinstein | |
| 2004/0266811 | A1 | 12/2004 | Weinstein | |
| 2008/0015236 | A1 * | 1/2008 | Weinstein | 514/364 |

OTHER PUBLICATIONS

Heber-Katz, E., The regenerating mouse ear, Semin Cell Dev Biol 10, 415-9 (1999).
Heber-Katz, E., Leferovich, J.M., Bedelbaeva, K. & Gourevitch, D., Spallanzani's Mouse: A Model of Restoration and Regeneration. Curr. Top Microbiol Immunol 280, 166-89 (2004).
Heber-Katz, E., et al. Regeneration in MRL Mice: Further Genetic Loci Controlling the Ear Hole Closure Trait using MRL and M.m. Castaneus Mice, Wound Repair Regen 12, 384-92 (2004).
Clark, L.D., Clark, R.K. & Heber-Katz, E., A New Murine Model for Mammalian Wound Repair and Regeneration, Clin Immunol Immunopathol 88, 35-45 (1998).
Ghazizadeh, S. & Taichman, L.B., Multiple classes of stem cells in cutaneous epithelium: a lineage analysis of adult mouse skin, Embo J 20, 1215-22 (2001).
Ferraris, C., Bernard, B.A. & Dhouailly, D., Adult epidermal keratinocytes are endowed with pilosebaceous forming abilities. Int J Dev Biol 41, 491-8 (1997).
Kaufman, M.H., The atlas of mouse development, xvi, 512 (Academic Press, London ; San Diego, 1992.

* cited by examiner

*Primary Examiner*—Raymond J Henley, III
(74) *Attorney, Agent, or Firm*—Dennis A. Bennett; Cynthia Hathaway (57) ABSTRACT

The present invention provides a use and method for GM284 to promote the regeneration of a bodily structure comprised of a composite tissue in a subject. Additionally, the present invention provides a use and method for GM284 to promote composite tissue regeneration in a subject. The present invention further provides a use and method for GM284 to promote the regeneration of cells of a composite tissue in a subject. Finally, the present invention provides a use and method for GM284 to treat an injury to a composite tissue in a subject in need of such treatment.

29 Claims, 7 Drawing Sheets

METHODS FOR PROMOTING COMPOSITE TISSUE REGENERATION AND USES THEREOF

RELATED APPLICATION

The present invention claims priority to U.S. Provisional No. 60/743,749 filed on 24 Mar. 2006, which is incorporated herein by reference in its entirety.

BACKGROUND OF THE INVENTION

1. Technical Field

This invention relates generally to a method for promoting the regeneration of composite tissues, and is particularly related to the use of the GM284 in such a method.

2. Related Art

Injured tissues are able to heal by regeneration, by repair, or by a combination of these processes. Regeneration results in the re-establishment of the original tissue structure and function. In contrast, tissue repair results in the replacement of the original tissue with a patch of connective tissue, or scar, which is functionally inferior to the original tissue. The response of most mammalian tissues to injury falls within a spectrum bounded by regeneration and repair.

In mammals and other higher organisms there is a failure of regeneration of composite or complex tissues. Bodily structures comprised of composite tissues, such as a limb or digit, or an appendage, such as an ear or nose, are made of numerous cell types arranged in an organized and iterative structure that is preserved from individual to individual. When composite tissues or bodily structures comprised of composite tissues are injured, regeneration requires the coordinated growth, and interactions of numerous cell types within the composite tissues to regenerate a bodily structure that effectively indistinguishable from the original.

The regeneration of composite tissues and entire body parts are biological capabilities shared by many lower species. For example, die starfish can regenerate entire limbs after amputations and the snail can regenerate its head. In contrast, most vertebrates have no ability to regenerate entire body parts. It is not clear if the inability of vertebrate composite tissues to regenerate represents a true inability to re-form these tissues following injury, or if the molecular and cellular mechanisms that control the processes have been re-directed for use in, other biological processes. The discovery presented herein by the inventor argues for the latter.

The MRL mouse is a spontaneously occurring mutant strain that differs from most mammals in that it regenerates composite tissue following injury. When a hole is placed through the ear of a wild-type mouse, there is little or no regeneration. In contrast, the placement of a full thickness hole through the ear of the MRL mouse results in complete regeneration of all the cell-types within the ear and the closure of the hole within 30 days (Heber-Katz, E., The regenerating mouse ear, *Semin Cell Dev Biol* 10, 415-9 (1999); Clark, L. D., Clark, R. K, & Heber-Katz, E., A new murine model for mammalian wound repair and regeneration, *Clin Immunol Immunopathol* 88, 35-45 (1998); Heber-Katz, E., Leferovich, J. M., Bedelbaeva, K. & Gourevitch, D. Spallanzani's mouse: a model of restoration and regeneration. *Curr Top Microbiol Immunol* 280, 165-89 (2004)).

Analysis of the genetic loci that are involved in this unique biology has demonstrated a complex set of traits that have been associated with 11 quantitative trait loci (Heber-Katz, E., et al. Regeneration in MRL mice: further genetic loci controlling the ear hole closure trait using MRL and M.m. Castaneus mice, *Wound Repair Regen* 12, 384-92 (2004)).

The regenerative capacity of the MRL mouse is not restricted to the ear, Cryoinfarction of the MRL mouse heart results in the anatomic and functional recovery of the heart, whereas there is no such regeneration in the wild-type heart in any mammalian species.

The inventor has previously shown that GM284, a non-immunosuppressive immunophilin ligand, promotes accelerated and extensive regeneration of skin following full-thickness lesions (U.S. patent application Ser. No. 10/290,657; Publication No. 20040092440) and of peripheral nerves following mechanical transection (U.S. patent application Ser. No. 10/290,654; Publication No. 20040026681).

The inventor tested the ability of GM284 to promote the regeneration of the composite tissues of the murine ear. The inventor has concluded from his experiments that GM284 activates a cascade of interactions that lock tissues in a state of regeneration. Moreover, the inventor's unexpected discovery suggests that these events are conserved across evolutionary lines, and that GM284 takes advantage of their existence in mammals.

SUMMARY OF THE INVENTION

The inventor demonstrates herein that treatment with GM284, a nonimmunosuppressive immunophilin ligand, beginning after a composite tissue in a bodily structure has been injured, results in the regeneration of the lost composite tissue and the regeneration of lost cells of the composite tissue. This is the first demonstration of a pharmacological intervention resulting in the regeneration of a mammalian bodily structure comprised of composite tissues following an injury thereto.

The present invention is based on the discovery by that GM284, beginning in the hours following a wound to a the ear of a mouse, and given daily for three weeks, results in the initiation of robust regeneration of the tissue lost by the wounding of the ear, as evidenced by histological, changes in the wound margins consistent with the regeneration thereof. This ability of GM284 is valuable and unexpected.

Consequently, the present invention provides:

1) a use for GM284 to promote the regeneration of a bodily structure comprised of composite tissue in a subject, wherein the GM284 is administered to the subject in an amount effective to promote the regeneration of the bodily structure in the subject;

2) a use of GM284 to promote composite tissue regeneration in a subject, wherein the GM284 is administered to the subject in an amount effective to promote regeneration of composite tissue in the subject;

3) a use of GM284 to promote the regeneration of cells of a composite tissue in a subject, wherein the GM284 is administered to the subject in an amount effective to promote the regeneration of cells of the composite tissue in the subject;

4) a use of GM284 to promote the regeneration of cells of a composite tissue, wherein the composite tissue is contacted with an amount of GM284 effective to promote the regeneration of cells of the composite tissue;

5) a use of GM284 to treat an injury to a composite tissue in a subject in need of treatment, wherein the GM284 is administered to the subject an amount effective to treat the injury to the composite tissue in the subject;

6) a method for promoting the regeneration of a bodily structure comprised of composite tissue in a subject, by administering to the subject an amount of GM284 effective to promote regeneration of the bodily structure in the subject;

7) a method for promoting the regeneration of composite tissue in a subject, by administering to the subject an amount of GM284 effective to promote regeneration of composite tissue in the subject;

8) a method for promoting the regeneration of cells of a composite tissue in a subject, by administering to the subject an amount, of GM284 effective to promote the regeneration of cells of the composite tissue;

9) a method for promoting the regeneration of cells of a composite tissue, by contacting the composite tissue with an amount of GM284 effective to promote the regeneration of cells of the composite tissue;

10) a method for treating an injury to a composite tissue in a subject in need of treatment, by administering to the subject an amount of GM284 effective to treat the injury to the composite tissue in the subject.

Additional aspects of the present invention will be apparent in view of the description that follows.

BRIEF DESCRIPTION OF THE FIGURES

FIG. 3 is comprised of four photographs of the dorsal aspects of the twice-punctured ears of a laboratory ICR mouse. The photographs forming a column on the left show the dorsal aspect of the twice-punctured ears of a mouse treated daily with vehicle. The photographs forming a column on the right show the dorsal aspect of the twice-punctured ears of a mouse treated daily with GM284. The upper row of photographs offers a comparison of the rate of composite tissue regeneration at one week post-lesioning. The lower row of photographs offers a comparison of the rate of composite tissue regeneration at two weeks post-lesioning.

In FIG. 4, the ordinate is labeled, "area remaining open" in the puncture wound and is scaled in relative units of area; and, the abscissa is labeled "days post-lesion-" Taller bars to the left at days 0, 7 and 14 represent vehicle-treated mice and shorter bars to the right at days 0, 7 and 14 represent GM284-treated mice.

FIG. 5 [upper portion] shows a low-power photomicrograph on the right [FIG. 5b] taken from tissue indicated by straight lines to the photograph of a wounded ear on the left [FIG. 5a]; and, [lower portion] shows a composite of two low-power photomicrographs on the right [FIG. 5d] taken from tissue indicated by straight lines pointing to the photograph of a wounded GM284-treated ear on the left [FIG. 5c].

In FIG. 7, image a. is microphotograph of a histological section of an intact mouse foot pad that has received a daily application of GM284. Image a. shows that the daily application of GM284 to the intact mouse footpad does not result in any readily identified alterations in the histological appearance of the tissues. Image b. is a microphotograph of a histological section of a mouse footpad in which a small incision has been made in the footpad prior to daily application of GM284. Image b. shows that the wounded tissue to which GM284 has been applied responds by generating numerous well formed sebaceous glands (arrows).

DETAILED DESCRIPTION OF THE INVENTION

The inventor has discovered that a nonimmunosuppressive ligand, termed GM284, that is known to enhance axonal regeneration and induce hypermyelination following mechanical transection of peripheral nerves, promotes the regeneration of composite tissue.

Figure 1:
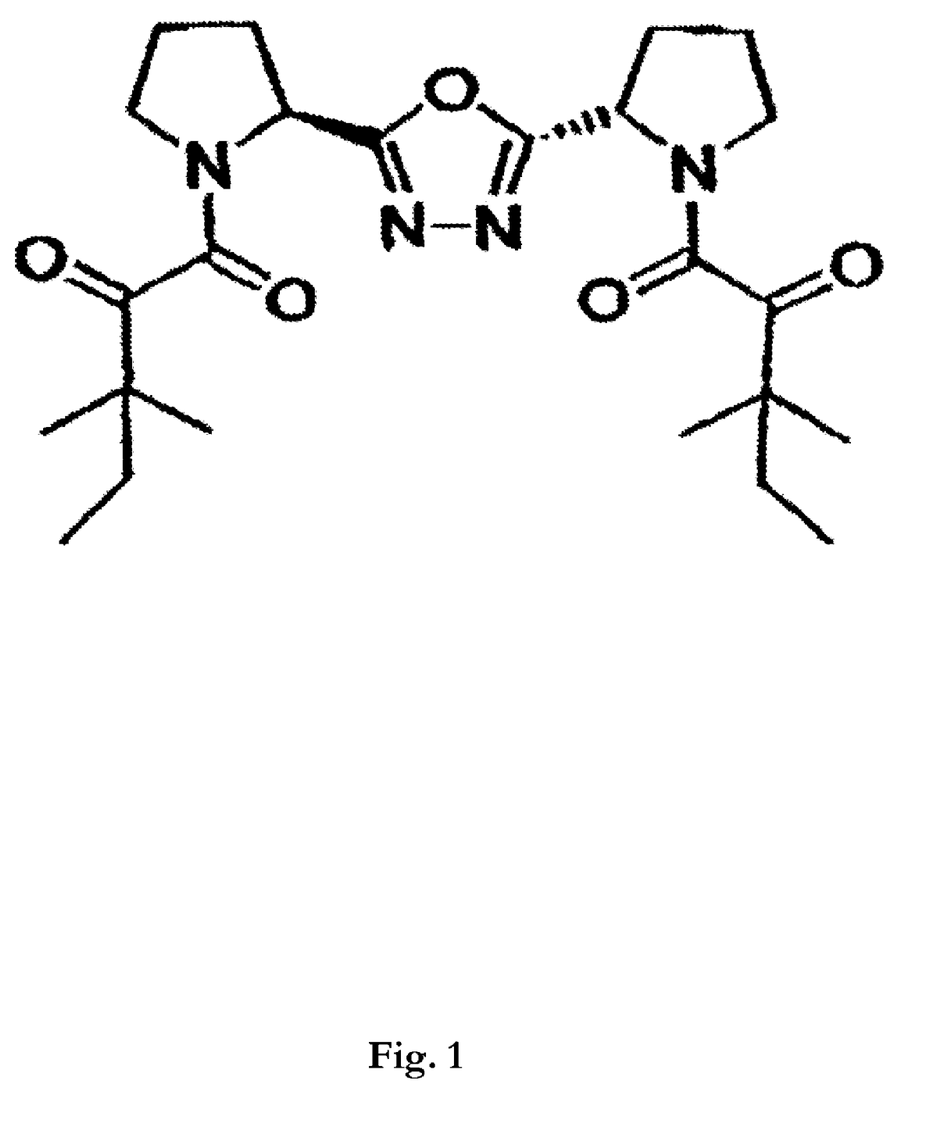
FIG. 1 is a schematic illustration of the chemical structure of GM284.

The structure of GM284 is depicted in FIG. 1, U.S. Pat. No. 6,809,107, entitled, "Neurotrophic pyrrolidines and piperidines, and related compositions and methods," issued to Kanojia, et al., on Oct. 26, 2004, and assigned to Ortho-McNeil Pharmaceutical, Inc. ("Ortho Patent '107"), which is herein incorporated by reference, discloses the composition and structure of GM284. GM284 may be prepared in accordance with method described in Ortho Patent '107. GM284 may be also administered for the uses and by the methods disclosed herein as a pro-drug.

It is believed that GM284 will be effective as a drug to treat injuries to composite tissue, as well as many types of disorders associated with diseases of composite tissue.

In the course of his experiments, the inventor discovered that injured composite tissue of the ears of mice treated topically with GM284 appeared dramatically different from those of vehicle-treated animals. The inventor's analysis demonstrates that the injured composite tissue of the ears of mice treated with GM284 healed by regeneration, as opposed to tailing to heal and as opposed to scarification, when compared with controls.

Accordingly, the present invention provides a method for promoting composite tissue regeneration, in a subject in need of such regeneration. As demonstrated herein, the GM284 has the ability to promote healing of a bodily structure comprised of composite tissue by promoting regeneration of the composite tissue from the margins of a wound that has excised composite tissue.

The amount of GM284 effective to promote healing of injured composite tissue in a subject in need thereof will vary depending upon the particular factors of each case, including the location and size of the injury to the composite tissue, the severity of the injury, the length of time to treatment, and the method of administration. This amount may be readily determined by the skilled artisan, based upon known procedures, including clinical trials, and methods disclosed herein.

As used herein, the term:

"composite tissue" refers to a combination of tissues, which, in the exemplary case of a limb, includes a "composite" of skin, muscles, bones, joints, nerves, blood vessels and connective tissue; and in the exemplary case of an ear includes a "composite" of skin, cartilage, nerves, blood vessels and hair follicles;

"bodily structure" refers to an aspect, part, portion or division of a mammalian body, such as, for example, a limb, a digit, an appendage, a feature, an organ, or an organ system that includes composite tissue;

"promoting regeneration of composite tissue" means augmenting, improving, increasing, or inducing partial or full growth or regrowth of composite tissue in a region of a bodily part, that includes injured composite tissue;

"growth" or "regrowth" refers to an increase in mass, volume, and/or thickness of composite tissue, and includes an increase in the proliferation of cell types of which the composite tissue is comprised.

Regeneration or enhanced regeneration of composite tissue in a region of a bodily part that includes injured composite tissue may be promoted, for example, by enhancing the regeneration of cell types of which the injured composite tissue is comprised. In a subject, the regeneration of composite tissue is promoted in the bodily part that includes the injured composite tissue; and, thus, contributes to the promotion of healing of the injured composite tissue in the subject.

The injury to the composite tissue may be the result of trauma, ischemia or any affliction (e.g., disease, injury, surgery) that eventuates in an injury to the composite tissue, such as, for example, and without limitation, laceration, avulsion, abrasion, amputation, crush, inflammation, infection, degeneration, degradation, dystrophy, destruction or atrophy.

The subject may be any animal, but is preferably a mammal (e.g., humans, domestic animals, and commercial animals). More preferably, the subject is a human.

In the method of the present invention, GM284 is administered to a subject in an amount effective to promote regeneration of injured composite tissue in the subject.

As used herein, the phrase "promote regeneration of injured composite tissue" means effective to ameliorate or moderate the tectonic impairment, functional impairment, clinical impairment, clinical appearance or clinical symptoms associated with an injury to composite tissue. For example, in an injury to composite tissue, the associated tectonic impairment, functional impairment, clinical impairment, clinical appearance or clinical symptoms may be ameliorated or moderated by inducing or accelerating the regeneration of cell, types comprising the injured composite tissue, In the present invention, the effective amount of GM284 is between about 1 µg/kg and about 100 µg/kg or between about 1 pM and about 100 pM.

The method of the present invention may be used to promote regeneration of composite tissue in a subject that includes the step of administering GM284 to the subject. The GM284 is administered to the subject in an amount effective to promote regeneration of the injured composite tissue in the subject, as defined above. In the present invention, the effective amount of GM284 is between about 1 µg/kg and about 100 µg/kg or between about 1 pM and about 100 pM.

The method of the present invention comprises contacting composite tissue with GM284. The composite tissue may be damaged or healthy/undamaged. The composite tissue may comprise a region of composite tissue that includes an injury.

The GM284 is contacted with composite tissue in an amount effective to promote regeneration of at least two of the cell-types of which the composite tissue is comprised. This amount may be determined by the skilled artisan using known procedures (e.g., concentration curves, ELISA, protein-concentration determination, radioimmunoassay, titration curves, and methods disclosed herein.

The method of the present invention may be used to promote regeneration of at least two of the cell-types of which the composite tissue is comprised in vitro, or in vivo in a subject. For example, GM284 may be contacted in vitro with facial tissue (e.g., a biopsy or plug of facial tissue removed from a subject) by introducing GM284 to the facial, tissue using conventional procedures. Alternatively, GM284 may be contacted in vivo with composite tissue in a subject by administering GM284 to the subject.

It is also within the confines of the present invention that GM284 may be introduced to composite tissue in vitro, using conventional procedures, to promote regeneration of cells-types of the composite tissue in vitro. Thereafter, the composite tissue may be introduced into a subject to provide cells-types of the composite tissue in vivo. In such an ex vivo approach, the composite tissue is preferably removed from the subject, subjected to introduction of GM284, and then reintroduced into the subject. The composite tissue cell-type regeneration promotes healing of an injured composite tissue in the subject.

Accordingly, the present invention provides a method for treating an injured composite tissue in a subject in need of treatment, comprising contacting the composite tissue in the subject with GM284 (e.g., by administering GM284 to the subject), thereby treating the injured composite tissue. Injured composite tissue that may be treated by methods disclosed herein include disorders characterized by injury of composite tissue cells. The GM284 is contacted with composite tissue in a subject (e.g., administered to a subject), for the purpose of treating an injured composite tissue, in an amount effective to promote regeneration of at least two cell-types of which the composite tissue is comprised.

According to the method of the present invention, GM284 may be administered to a human or animal subject by known procedures, including, without limitation, oral administration, parenteral administration (e.g., epifascial, intracapsular, intracutaneous, intradermal, intramuscular, intraorbital, intraperitoneal, intraspinal, intrasternal, intrathecal, intravascular, intravenous, parenchymatous, or subcutaneous administration), sublingual administration, topical administration, transdermal administration, and administration through an osmotic mini-pump. Preferably, GM284 is administered topically.

For oral administration, the formulation of the GM284 may be presented as capsules, tablets, powders, granules, or as a suspension. The formulation may have conventional additives, such as lactose, mannitol, cornstarch, or potato starch. The formulation also may be presented with binders, such as crystalline cellulose, cellulose derivatives, acacia, cornstarch, or gelatins. Additionally, the formulation may be presented with disintegrators, such as cornstarch, potato starch, or sodium carboxymethylcellulose. The formulation also may be presented with dibasic calcium phosphate anhydrous or sodium starch glycolate. Finally, the formulation may be presented with lubricants, such as talc or magnesium stearate.

For parenteral administration (i.e., administration by injection through a route other than the alimentary canal), the GM284 may be combined with a sterile aqueous solution that is preferably isotonic with the blood of the subject. Such a formulation may be prepared, by dissolving a solid active ingredient in water containing physiologically-compatible substances, such as sodium chloride, glycine, and the like, and having a buffered pH compatible with physiological conditions, so as to produce an aqueous solution, then rendering said solution sterile. The formulations may be presented in unit or multi-dose containers, such as sealed ampoules or vials. The formulation may be delivered by any mode of injection, including, without limitation, epifascial, intracapsular, intracranial, intracutaneous, intramuscular, intraorbital, intraperitoneal, intraspinal, intrasternal, intrathecal, intravascular, intravenous, parenchymatous, or subcutaneous.

For transdermal administration, the GM284 may be combined with skin penetration enhancers, such as propylene glycol, polyethylene glycol, isopropanol, ethanol, oleic acid, N-methylpyrrolidone, dimethyl sulfoxide, and the like, which, increase the permeability of the skin to the GM284, and permit the GM284 to penetrate through the skin and into the bloodstream. The ligand/enhancer compositions also may be further combined with a polymeric substance, such as ethylcellulose, hydroxypropyl cellulose, ethylene/vinylacetate, polyvinyl pyrrolidone, and the like, to provide the composition in gel form, which may be dissolved in solvent, such as methylene chloride, evaporated to the desired viscosity, and then applied to backing material to provide a patch. GM284 may be administered transdermally at the site of an injury to the subject where trauma has occurred, or where the injury is localized. Alternatively, GM284 may be administered transdermally at a site other than the affected area, in order to achieve systemic administration.

For topical administration, the GM284 may be combined with additional materials that are known for use in skin-care products, or which are otherwise suitable for topical application. Such optional materials include, but are not limited to, disbursing agents, masking agents, preservatives, processing agents, and additives having specific physicochemical properties, such as polymeric film formers and the like.

GM284 may also be released or delivered from an osmotic mini-pump or other time-release device. The release rate from an elementary osmotic mini-pump may be modulated with a microporous, fast-response gel disposed in the release orifice. An osmotic mini-pump would be useful for controlling release, or targeting delivery, of the GM284.

It is within the confines of the present invention that a formulation containing GM284 may be further associated with a pharmaceutically acceptable carrier, thereby comprising a pharmaceutical composition. Accordingly, the present invention further provides a pharmaceutical composition, comprising GM284 and a pharmaceutically acceptable carrier. The pharmaceutically acceptable carrier must be "acceptable" in the sense of being compatible with the other ingredients of the composition, and not deleterious to the recipient thereof. Examples of acceptable pharmaceutical carriers include carboxymethylcellulose, crystalline cellulose, glycerin, gum arable, lactose, magnesium stearate, methyl cellulose, powders, saline, sodium alginate, sucrose, starch, talc, and water, among others. Formulations of the pharmaceutical composition may be conveniently presented in unit dosage.

The formulations of the present invention may be prepared by methods well known in the pharmaceutical arts. For example, GM284 may be brought into association with a earner or diluent, as a suspension or solution. Optionally, one or more accessory ingredients (e.g., buffers, flavoring agents, surface active agents, and the like) also may be added. The choice of carrier will depend upon the route of administration. The pharmaceutical composition would be useful, for administering the GM284 of the present invention to a subject to promote regeneration of an injured composite tissue. The GM284 is provided, in an amount that is effective to promote regeneration of the injured, composite tissue in a subject to whom the pharmaceutical composition is administered. That amount may be readily determined by the skilled artisan, as described above.

The present, invention also provides a method, for promoting regeneration of composite tissue in a subject. As described above, regeneration of composite tissue in a subject may be promoted by enhancing proliferation of cells of the composite tissue in the subject. Accordingly, in one embodiment of the invention, the regeneration of composite tissue is promoted at the site of an injury to a composite tissue in the subject, and, thus, contributes to the promotion of healing of the composite tissue in the subject.

The present invention is described the following example, which is set forth to aid in the understanding of the invention, and should not be construed, to limit in any way the scope of the invention as defined in the claims which follow thereafter.

EXAMPLE

Experimental Methods

All mice used herein were retired ICR breeders. The animals were anesthetized with an intraperitoneal injection of 200 µl of 5% Tribromoethanol (Avertin®). When anesthesia was attained, the ears were cleaned with alcohol and [either one or] two holes about 3 mm in diameter were punched into the ear using a standard ear punch intended for use in permanently identifying animals. The ear was chosen as the animal structure to be wounded because it is comprised of a composite tissue including cells of the epidermis and dermis, chondrocytes, hair follicle cells, and cells of the vasculature system.

The wounded animals were returned to their cages and treatment with GM284 was begun, within 2 hours of the surgery.

FIG. 1 shows a schematic illustration of the chemical structure of GM284. GM284 was diluted to a final concentration of 10 nM in diluent ("vehicle") of a 30% MeOH/70% polypropylene glycol, solution. As diluted, 5 µl of GM284 was applied topically once daily to both the ventral side and dorsal side of an ipsilateral twice-punctured ear of each mouse. The contralateral twice-punctured ear of each mouse received a topical application of 5 µl of vehicle to both the ventral side and dorsal side. These mice formed a first group.

In a second group, treatment was applied unilaterally using, 5 µl of GM284 applied topically once daily to both the ventral side and dorsal side of an ipsilateral twice-punctured ear of each mouse. The contralateral twice-punctured ear of each mouse received no treatment.

In a third group, treatment, was applied unilaterally using 5 µl of vehicle applied topically once daily to both the ventral side and dorsal side of an ipsilateral twice-punctured ear of each mouse. The contralateral twice-punctured ear of each mouse received no treatment.

All groups of animals were maintained under standard conditions.

In order to monitor the progress of composite tissue, regeneration or a failure thereof, the animals were anesthetized and photographed, to compare the size of their lesions on the $7^{th}$ and $14^{th}$ post-lesion days.

At the completion of the experiments, all of the animals were sacrificed with an overdose of Avertin®. All of the ears were harvested and immersion fixed in 4% paraformaldehyde in phosphate buffeted saline (PBS) overnight at 4° C., followed by cryoprotection in 30% sucrose and sectioning at 10 micra through the lesion sites. The sections were stained with H&E and viewed with an Olympus BX60 light, microscope.

In the first group of animals, GM284 was applied topically once pet day unilaterally to an ipsilateral ear of following the placement of two holes in each ear. The contralateral ear was treated with vehicle.

Figure 2:
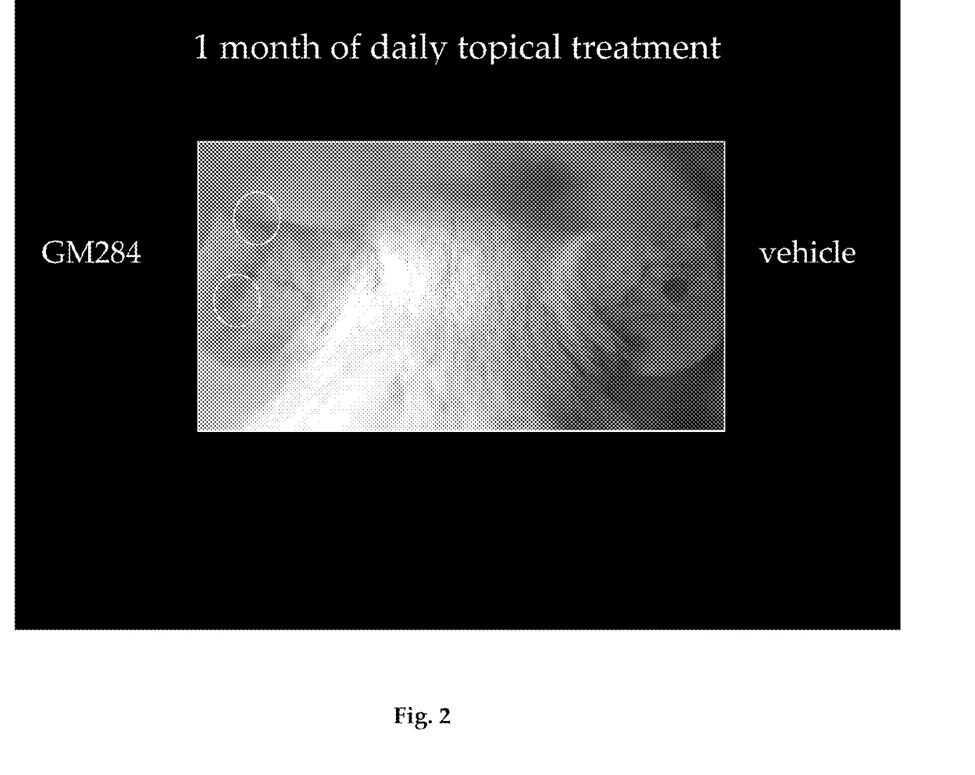
FIG. 2 is a photograph of dorsal aspects of the ears of an ICR laboratory mouse one month after the placement of full-thickness holes into both ears, followed by daily topical administration of GM284 to the dorsal and ventral aspects of the left, ear and daily topical administration of vehicle to the dorsal and ventral aspects of the right, ear.
Figure 3A:
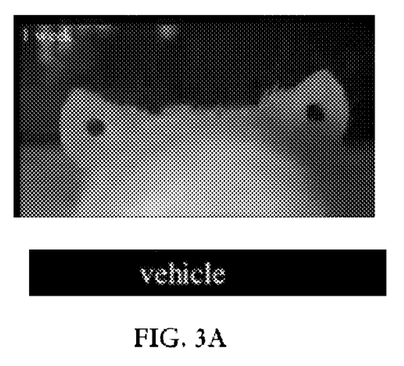
FIG. 3A shows the rate of composite tissue regeneration of twice-punctured ears of a laboratory ICR mouse treated with a vehicle at 1 week.
Figure 3B:
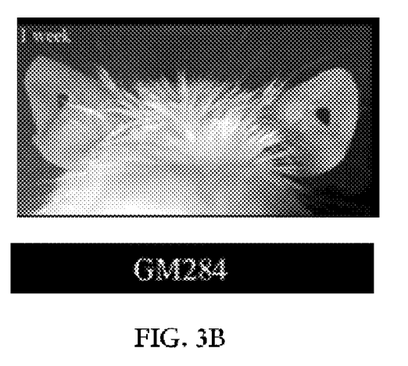
FIG. 3B shows the rate of composite tissue regeneration of twice-punctured ears of a laboratory ICR mouse treated with a GM284 at 1 week.
Figure 3C:
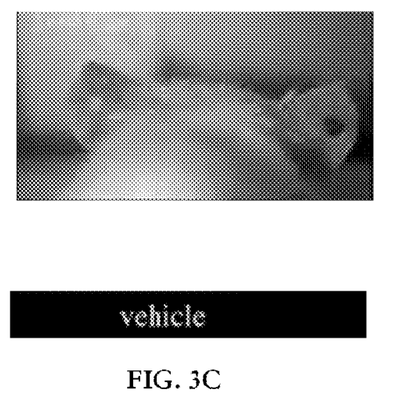
FIG. 3C shows the rate of composite tissue regeneration of twice-punctured ears of a laboratory ICR mouse treated with a vehicle at 2 weeks.
Figure 3D:
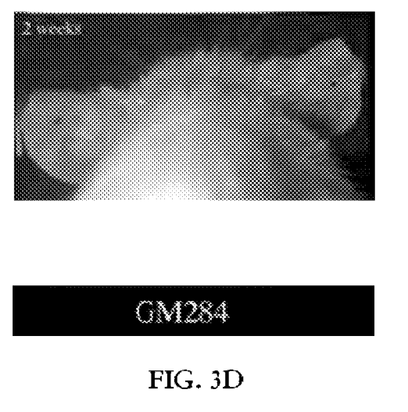
FIG. 3D shows the rate of composite tissue regeneration of twice-punctured ears of a laboratory ICR mouse treated with a GM284 at 2 weeks.

FIG. 2 is a photograph of dorsal aspects of the ears of an ICR laboratory mouse one month after the placement of full-thickness holes into both ears, followed by daily topical administration of GM284 to the dorsal and ventral aspects of the left ear and daily topical administration of vehicle to the dorsal and ventral aspects of the right ear.

As shown in FIG. 2, the holes in the left ear responded to treatment with GM284 by closing. In contrast, the holes in the contralateral right ear, treated with the vehicle only, remain open, suggesting that the actions of GM284 are local, mediated by the interactions of the drug with the local environment. FIG. 2 shows that GM284 induces regeneration of composite tissues through local actions.

FIG. 3 is comprised of four photographs of the dorsal aspects of the twice-punctured ears of a laboratory ICR mouse. The photographs forming a column on the left, show the dorsal aspect of the twice-punctured ears of a mouse treated, daily with vehicle. The photographs forming a column on the right show the dorsal aspect of the twice-punctured ears of a mouse treated daily with GM284. The upper row of photographs offers a comparison of the rate of composite tissue wound regeneration at one week post-lesioning. The lower row of photographs offers a comparison of the rate of composite tissue wound regeneration at two weeks post-lesioning.

FIG. 3 demonstrates that as early as one week following lesioning, the GM284-treated composite tissue of the right ear showed significant regeneration, whereas the vehicle-treated composite tissue of the left ear showed virtually no signs of regeneration (compare the upper row of photographs in FIG. 3), FIG. 3 further demonstrates that at two weeks following lesioning, the GM284-treated composite tissue of the right ear showed near complete regeneration, whereas the vehicle-treated composite tissue of the left ear continued, to show virtually no signs of regeneration (compare the lower row of photographs in FIG. 3).

Quantitation, of the extent of tissue regeneration [at one week] revealed that the GM284-treated composite tissue of the right ear regenerated to an extent that left about ⅔ of the area of the original wound open, whereas the vehicle-treated ears remain unchanged. As shown in FIG. 3, the lesions are 95% closed by the 14$^{th}$ day of treatment, while no significant regeneration is seen in the control animals. Treatment with GM284 rapidly induced composite tissue regeneration Inspection revealed that holes in the vehicle-treated mouse ears did not close under baseline conditions. Rather the edge of the untreated wound takes on the appearance of scar tissue.

Figure 4:
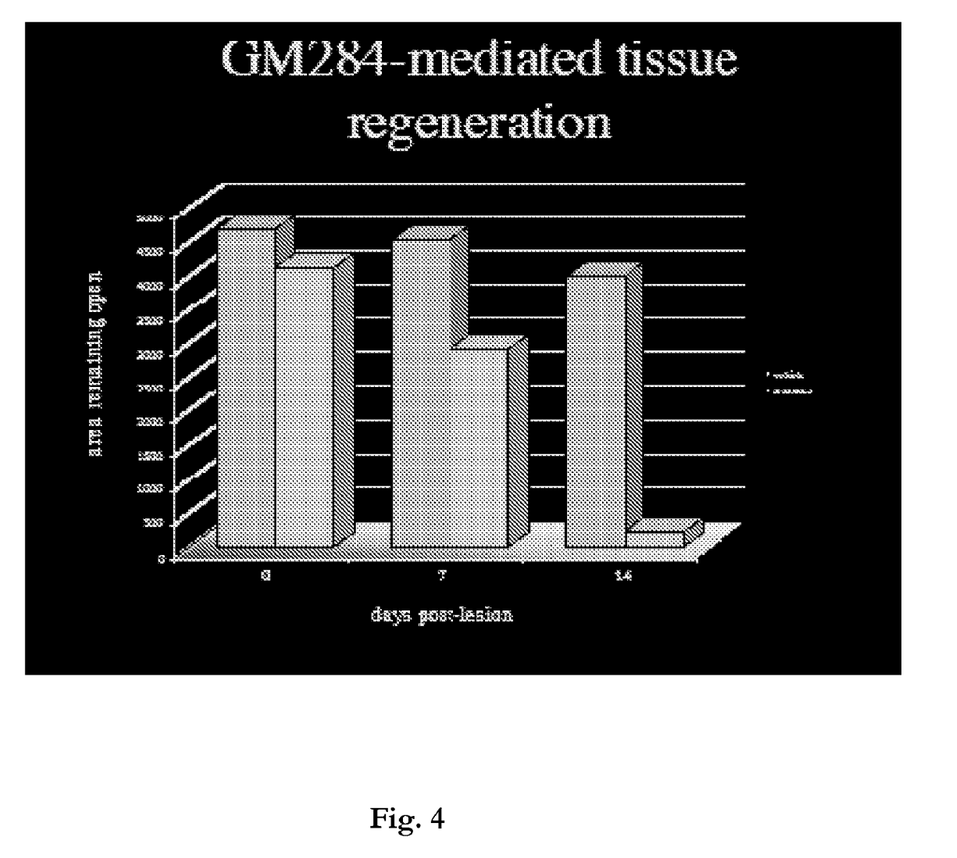
FIG. 4 shows a bar graph illustrating the relative rates of full-thickness puncture wound closure in GM284-treated and vehicle-treated mice.
Figure 5A:
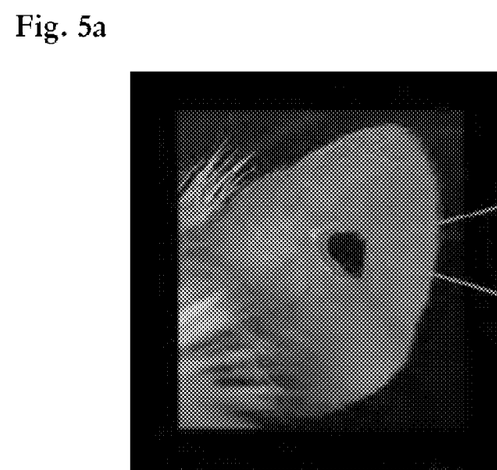
Figure 5B:
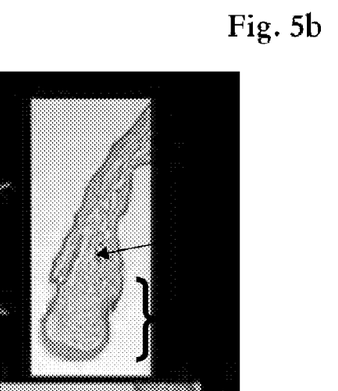
Figure 5C:
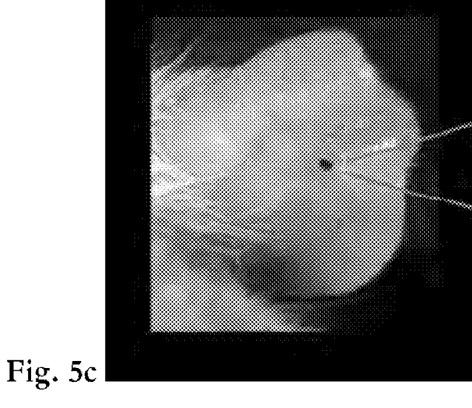
Figure 5D:
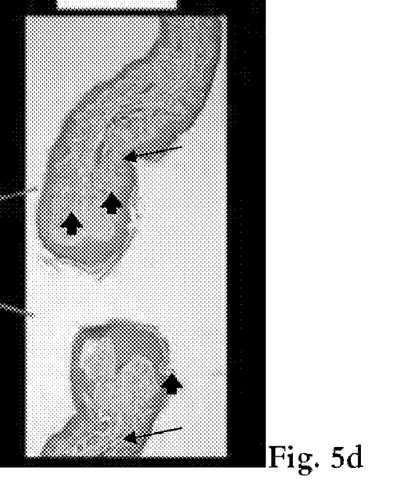

FIG. 4 shows a bar graph illustrating the relative rates of full-thickness puncture wound closure in GM284-treated and vehicle-treated mice. In FIG. 4, the ordinate is labeled "area remaining open" in the puncture wound and is scaled in relative units of area; and, the abscissa is labeled "days post-lesion." Taller bars to the left at days 0, 7 and 14 represent vehicle-treated mice and shorter bars to the right at days 0, 7 and 14 represent GM284-treated mice. FIG. 4 demonstrates that at 14 days post-lesion the area of wounding in GM284-treated mice has all but closed; whereas, the area of wounding in vehicle-treated mice has decreased insubstantially.

FIG. 5 [upper portion] shows a low-power photomicrograph on the right taken from tissue indicated by straight lines pointing to the photograph of a wounded ear on the left; and, [lower portion] shows two low-power photomicrographs on the right taken from tissue indicated by straight lines pointing to the photograph of a wounded GM284-treated ear on the left. The area in the curly bracket in the upper left micrograph shows the area of scar formation in the vehicle treated ear, which is absent in the drug-treated tissue. The thin arrows point to the band of chondrocytes that run down the middle of the ear, which have regenerated up to the distal-most end of the treated ear, and the thick arrowheads show newly generated blood vessels in the distal, regenerated ear.

Histological analysis of the GM284-treated composite tissue demonstrates a remarkable degree of regeneration of the complex component's of the ear, how-power micrographs, such as those shown in FIG. 5 [lower portion], reveal that both of the leading edges of the GM284-treated ear are visible, as they have regenerated sufficiently that, both are visible in the same microscopic field. In contrast, in FIG. 5 [upper portion], only one side of the vehicle-treated tissue can be seen in the micrograph at the same magnification clue to a failure to regenerate.

Even at the low-power microscopy of FIG. 5, a scar is visible at the distal end of the vehicle-treated tissue [upper portion, bracketed area on right], which is filled with amorphic, fibrotic material. By contrast, the distal aspects of the GM284-treated composite tissue is well-formed, with clearly identifiable tissues within the growing ear. The regenerated tissues include a band of chondrocytes growing in the middle of the ear, intact dermis and epidermis, and blood vessels that grow up to the distal end of the ear bud.

Figure 6:
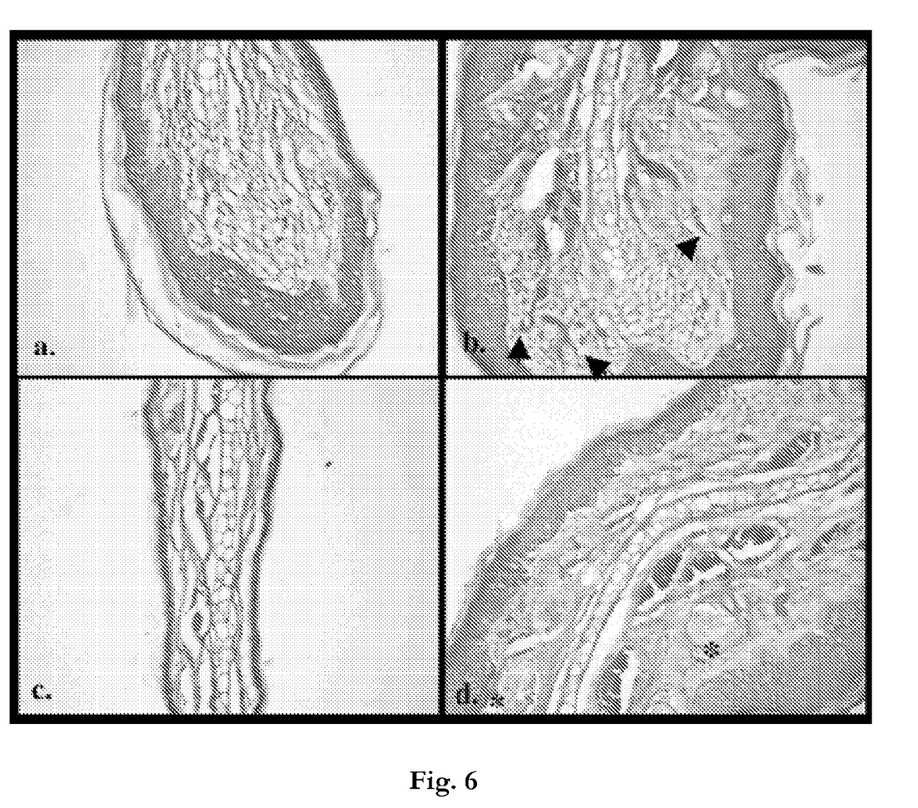
FIG. 6 is a set of four high-power photomicrographs a., b., c. and d., demonstrating that a full complement of regenerated tissue-types is present within a GM284-treated ear. Micrographs a. and c, are control, vehicle treated tissue; micrographs b. and d. are GM284 treated tissue. The triangular arrowheads point to newly formed blood vessels; asterisk marks sebaceous glands present in the newly regenerated tissue.

FIG. 6 is a set of four high-power photomicrographs a., b., c. and c., demonstrating that a full complement of regenerated tissue-types are present within a GM284-treated ear. Micrographs a. and c, are control, vehicle treated tissue; micrographs b. and d. are GM284 treated tissue. The triangular arrowheads point, to newly formed blood vessels; asterisk marks sebaceous glands present in the newly regenerated tissue.

In FIG. 6:
a) photomicrograph a. shows the scar-containing stump of the vehicle treated ear;
b) photomicrograph b. shows regenerated cartilage that has grown to the very distal end of a GM284-treated ear. Adjacent to the new cartilage there are numerous small blood vessels that have regenerated as well [triangular arrow-heads], which are not seen in the distal-most region of the vehicle-treated tissue;
c) photomicrograph c. shows a band of chondrocytes that runs through the middle of an undamaged region of a vehicle-treated ear; and,
d) photomicrograph d. shows the regeneration of sebaceous glands [asterisks] in a GM284-treated ear.

Taken together, these data demonstrate that treatment with GM284 results in the full regeneration of the composite tissues of the ear.

Figure 7:
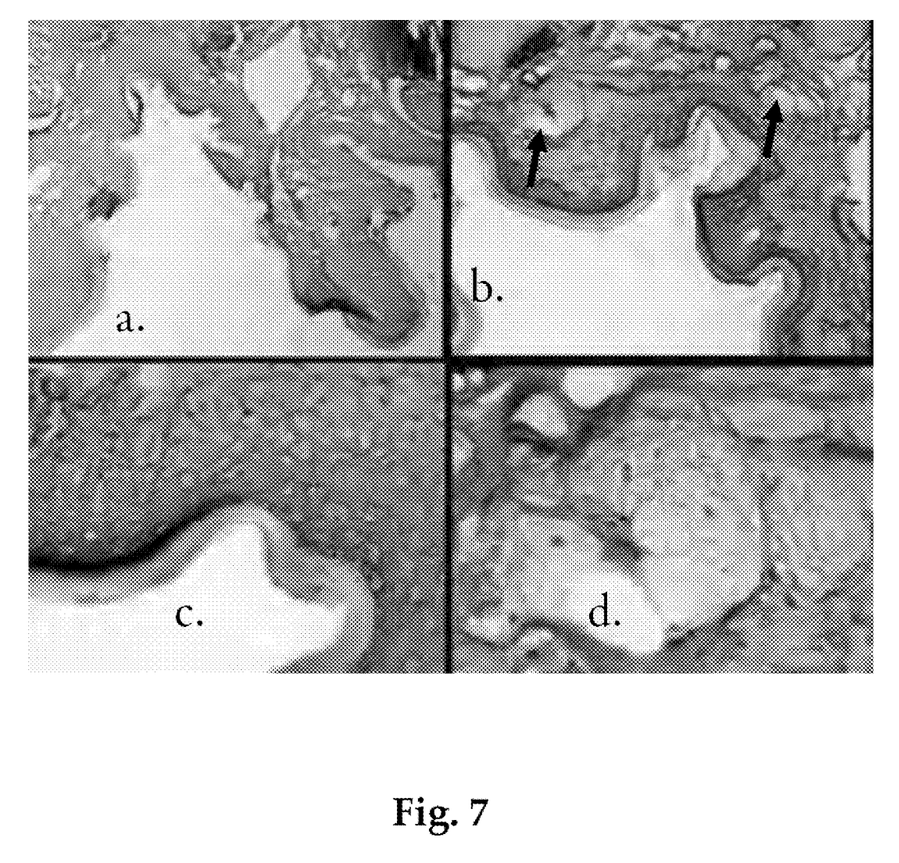
FIG. 7 is a set of four photomicrographs of a mouse foot-pad. Micrographs a. and b. are low power (4×) images; micrographs c. and d. are higher power images (20×) of the same region.

FIG. 7 is a set of four photomicrographs of a mouse footpad. Micrographs a. and b. are low power (4×) images; micrographs c. and d. are higher power images (20×). In FIG. 7, image a. is microphotograph of a histological section of an intact mouse foot pad that has received a daily application of GM284. Image a. shows that the daily application of GM284 to the intact mouse footpad does not result in any readily identified alterations in the histological appearance of the tissues.

In FIG. 7, image b. is a microphotograph of a histological section of a mouse footpad in which a small incision has been made in the footpad prior to daily application of GM284. Image b. shows that the wounded tissue to which GM284 has been applied responds by generating numerous well formed sebaceous glands.

These findings are significant in that the mouse foot, pad, much like the palm of the human hand, is glabrous, and, as such, it is normally without these structures. These finding are also consistent with observations that treatment with GM284 induces structures that are thought to be the normal repository of skin stem cells (Ghazizadeh, S. & Taichman, L. B., Multiple classes of stem cells in cutaneous epithelium: a lineage analysis of adult mouse skin, *Embo J* 20, 1215-22 (2001); Ferraris, C., Bernard, B. A. & Dhouailly, D., Adult epidermal keratinocytes are endowed with pilosebaceous forming abilities. *Int J Dev Biol* 41, 491-8 (1997)).

The foregoing unexpected results demonstrate that, topical application of GM0284 results in the regeneration of the mouse ear, a composite structure that comprises cartilage, blood vessels and skin, with a full compliment of intradermal structures.

The foregoing unexpected results expand the therapeutic potential of GM284 beyond the inventor's previous showing that treatment of damaged tissues with GM284 results in anatomical regeneration as well as restoration of physiological function, including the regeneration of skin (dermis, epidermis and intradermal structures), U.S. Publication No. 20040092440, the regeneration of cardiac myocytes following ischemia, U.S. application Ser. No. 11/670,964, and the regeneration of sensory and motor nerves U.S. Publication No. 20040026681.

Importantly, there are no observed anatomical, histological or functional effects of GM284 on normal, undamaged tissue, suggesting that GM284 exerts its regenerative effects preferentially—only on damaged tissue—and to the exclusion of scarring.

The foregoing unexpected results are in contradistinction to the scarring and disfigurement that ensues when the ear is untreated or vehicle-treated.

While regeneration often phenocopies some aspects of development, the two biological processes differ in significant ways. These differences are especially apparent in the regeneration of composite tissue. In the case of the ear, the tissue develops en toto from an anlage of the ear bud first seen at day 11.5 of mouse embryonic development (Kaufman, M. H., *The Atlas of Mouse Development*, xvi, 512 (Academic Press, London; San Diego, 1992)), with each, tissue type entering in stereotyped manner.

In contrast, the wounded composite tissue created at the margins of the holes punched in the mouse ears that are the subject of this disclosure, which regenerates to closure under the influence of GM284, does so in an environment that is very different from the E11.5 ear bud. The regeneration of the wounded composite tissues requires that each of the cell-types in the affected area respond both by proliferating and by interacting with the other cell-types to repopulate the excised tissues in a highly organized manner.

One hypothesis for this capability is that the needed cell-types are recruited from, distal reserves to repopulate damaged regions. Another hypothesis is that GM284 acts locally to alter the proliferative and cell-fate choices of proximal cell-types to repopulate damaged regions. The inventor's finding that GM284 acts locally is consistent with the later hypothesis. It is likely that GM284 acts to accelerate cell-cell interactions that mediate regeneration.

GM284 has no functional or histological effects on undamaged tissues supports our hypothesis that GM284 acts preferentially on damaged composite tissues to drive them into a regenerative rather that forming scar tissue.

GM284 promotes composite tissue regeneration to contribute to the reformation of intact composite tissues that is substantially indistinguishable in appearance and function from normal, undamaged tissue.

While the foregoing invention has been described in some detail for purposes of clarity and understanding, it will be appreciated by one skilled in the art, from a reading of the disclosure that various changes in form and detail can be made without departing from the true scope of the invention in the appended claims.

What is claimed is:

1. A method for promoting the regeneration of a bodily structure comprised of composite tissues having at least one non-epidermal, non-neural component in a subject, comprising the step of administering to the subject an amount of GM284 effective to promote the regeneration of the bodily structure in the subject.

2. The method of claim 1, wherein, the regeneration of the bodily structure is promoted in the subject by promoting composite tissue regeneration.

3. The method of claim 2, wherein the regeneration of the bodily structure in the subject is promoted by regenerating cells of the composite tissue.

4. The method of claim 1, wherein, the subject is a mammal.

5. The method, of claim 4, wherein the mammal is a human.

6. The method of claim 1, wherein the amount of GM284 is between about 1 µg/kg and about 1.00 µg/kg, inclusive of the indicated dosage endpoints.

7. The method of claim 1, wherein die amount of GM284 is between about 1 mg/kg and 5 mg/kg, inclusive of the indicated dosage endpoints.

8. The method of claim 1, wherein the amount of GM284 is between about 1 pM and about 100 pM, inclusive of the indicated dosage endpoints.

9. The method of claim 1, wherein the GM284 is administered to the subject by oral administration, parenteral administration, sublingual administration, topical administration, trans-dermal administration, or osmotic pump.

10. A method for promoting composite tissue having at least one non-epidermal, non-neural component in a subject, comprising the step of administering to the subject an amount of GM284 effective to promote composite tissue regeneration in the subject.

11. The method of claim 10, wherein the composite tissue regeneration in the subject is promoted by promoting regeneration of cells of the composite tissue in the subject.

12. The method of claim 11, wherein the composite tissue regeneration is promoted in the region of an injury to a composite tissue in the subject.

13. The method of claim 10, wherein the subject is a mammal.

14. The method of claim 13, wherein the mammal is a human.

15. The method of claim 12, wherein the amount of GM284 is between about 1 µg/kg and about 100 µg/kg. inclusive of the indicated dosage endpoints.

16. The method of claim 12, wherein the amount of GM284 is between about 1 mg/kg and about 5 µg/kg, inclusive of the indicated dosage endpoints.

17. The method of claim 12, wherein the amount of GM284 is between about 1 pM and about 100 pM, inclusive of the indicated dosage endpoints.

18. The method of claim 12, wherein the GM284 is administered to the subject by oral administration, parenteral administration, sublingual administration, topical administration, transdermal administration, or osmotic pump.

19. A method for promoting the regeneration of cells of a composite tissue having at least one non-epidermal, non-neural component, comprising contacting the composite tissue with an amount of GM284 effective to promote the regeneration of cells of the composite tissue.

20. The method of claim 19, wherein the contacting is effected in vitro.

21. The method of claim 19, wherein the contacting is effected in vivo in a subject.

22. The method of claim 21, wherein the regeneration of cells of the composite tissue promotes healing of a wound in the composite tissue in the subject.

23. The method of claim 19, wherein the contacting is effected in vivo in a subject by administering GM284 to the subject.

24. The method of claim 23, wherein the GM284 is administered to the subject by oral administration, parenteral administration, sublingual administration, topical administration, transdermal administration, or osmotic pump.

25. The method of claim 21, wherein the subject is a mammal.

26. The method of claim 25, wherein the mammal is a human.

27. The method of claim 26, wherein the human has an injury to tire composite tissue.

28. The method of claim 24, wherein the amount of the GM284 is between about 1 pM and about 100 pM, inclusive of the indicated dosage endpoints.

29. A method for treating an injury to a composite tissue having at least one non-epidermal, non-neural component in a subject in need of treatment, comprising administering to the subject an amount of GM284 effective to treat the injury to the composite tissue in the subject.

* * * * *